United States Patent
Hobbs et al.

(10) Patent No.: US 7,347,852 B2
(45) Date of Patent: Mar. 25, 2008

(54) CATHETER RETENTION

(75) Inventors: Eamonn P. Hobbs, Queensbury, NY (US); William M. Appling, Granville, NY (US); Angelo J. Tarricone, Lake Luzerne, NY (US); Theodore J. Beyer, Queensbury, NY (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 09/989,261

(22) Filed: Nov. 20, 2001

(65) Prior Publication Data

US 2003/0097091 A1   May 22, 2003

(51) Int. Cl.
  *A61M 25/00* (2006.01)
(52) U.S. Cl. .......................... 604/523; 604/43
(58) Field of Classification Search ................ 604/523, 604/532–535, 539, 284, 164.05, 174, 177, 604/179, 180, 43, 508; 138/115, 117
See application file for complete search history.

(56) References Cited

U.S. PATENT DOCUMENTS

| | | | |
|---|---|---|---|
| 4,778,448 A | * | 10/1988 | Meer .......................... 604/533 |
| 4,850,358 A | * | 7/1989 | Millar ......................... 600/486 |
| 5,053,023 A | | 10/1991 | Martin |
| 5,718,692 A | | 2/1998 | Schon et al. |
| 5,947,953 A | | 9/1999 | Ash et al. |
| 6,001,079 A | | 12/1999 | Pourchez |
| 6,117,117 A | * | 9/2000 | Mauch ........................ 604/284 |
| 6,749,628 B1 | * | 6/2004 | Callol et al. ................ 623/1.15 |
| 2004/0167463 A1 | * | 8/2004 | Zawacki et al. .............. 604/43 |
| 2005/0054990 A1 | * | 3/2005 | Graft et al. .................. 604/284 |

* cited by examiner

Primary Examiner—Kevin C. Sirmons
Assistant Examiner—Laura C. Schell
(74) Attorney, Agent, or Firm—Cowan, Liebowitz & Latman, P.C.

(57) ABSTRACT

A multiple tube catheter, such as a hemo-dialysis catheter, has first and second tubes which are attached to each other over a zone by one or more longitudinally extending wires which joins the two tubes over that zone. When a catheter is implanted in the patient, the attached zone is within the patient so that the catheter cannot be removed or advanced. When the catheter is to be removed, the longitudinally extending wire or wires are pulled proximally out of the tubes involved so that the two tubes can be separated and individually removed. A flexible separating prong within the patient and proximal of the zone holds the tubes apart to further assure that the catheter cannot be moved.

19 Claims, 9 Drawing Sheets

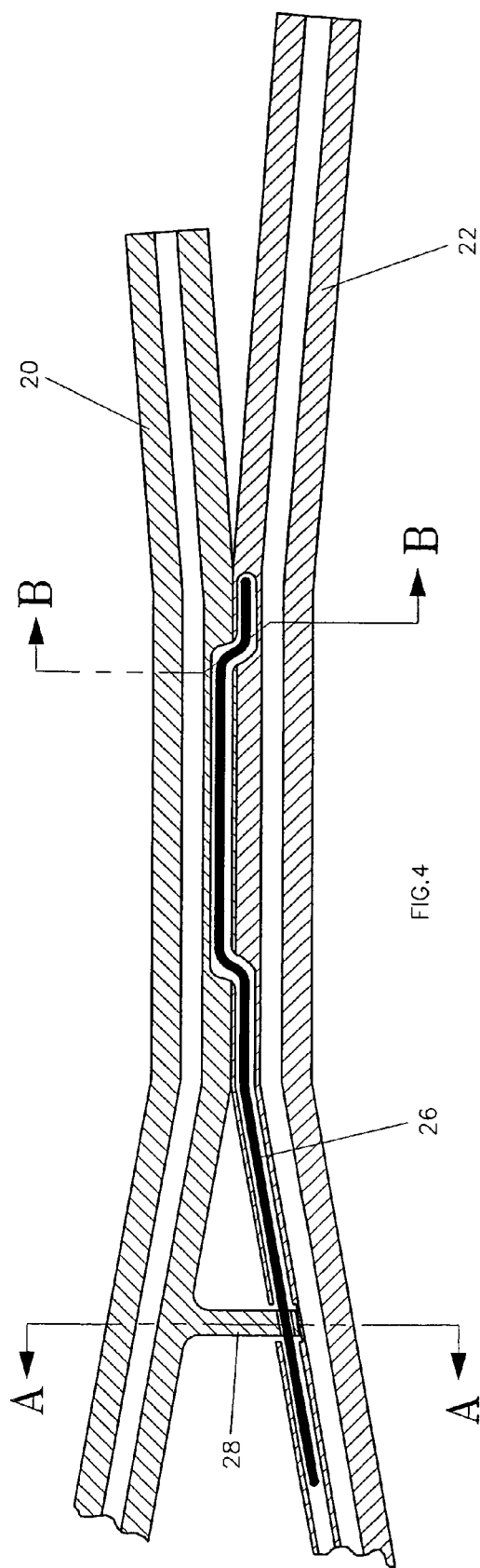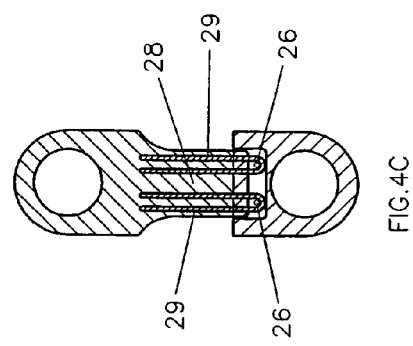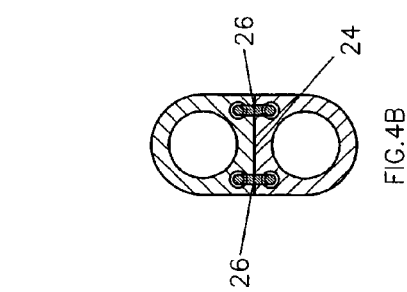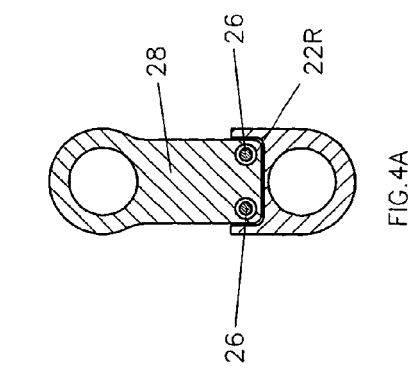

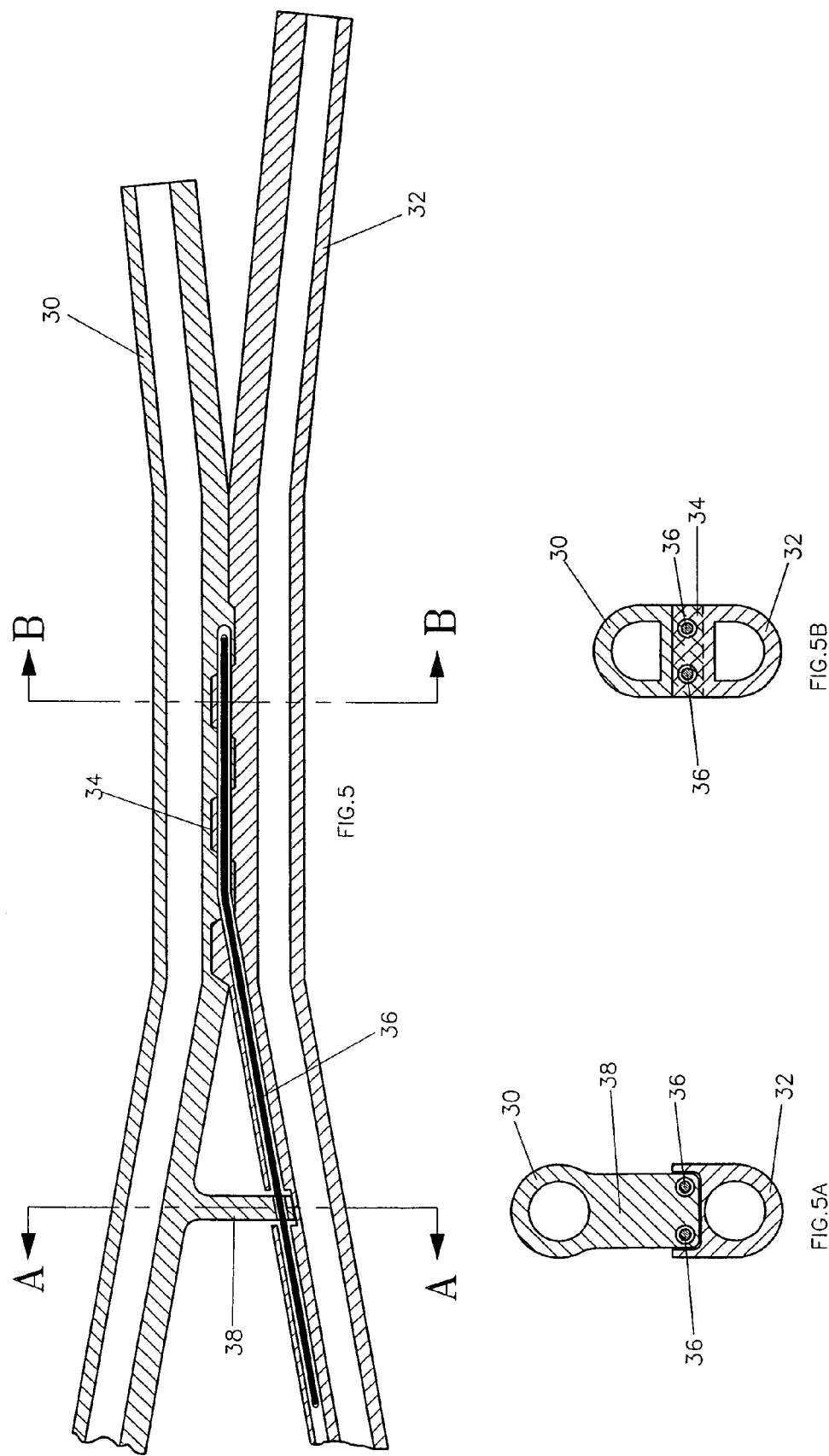

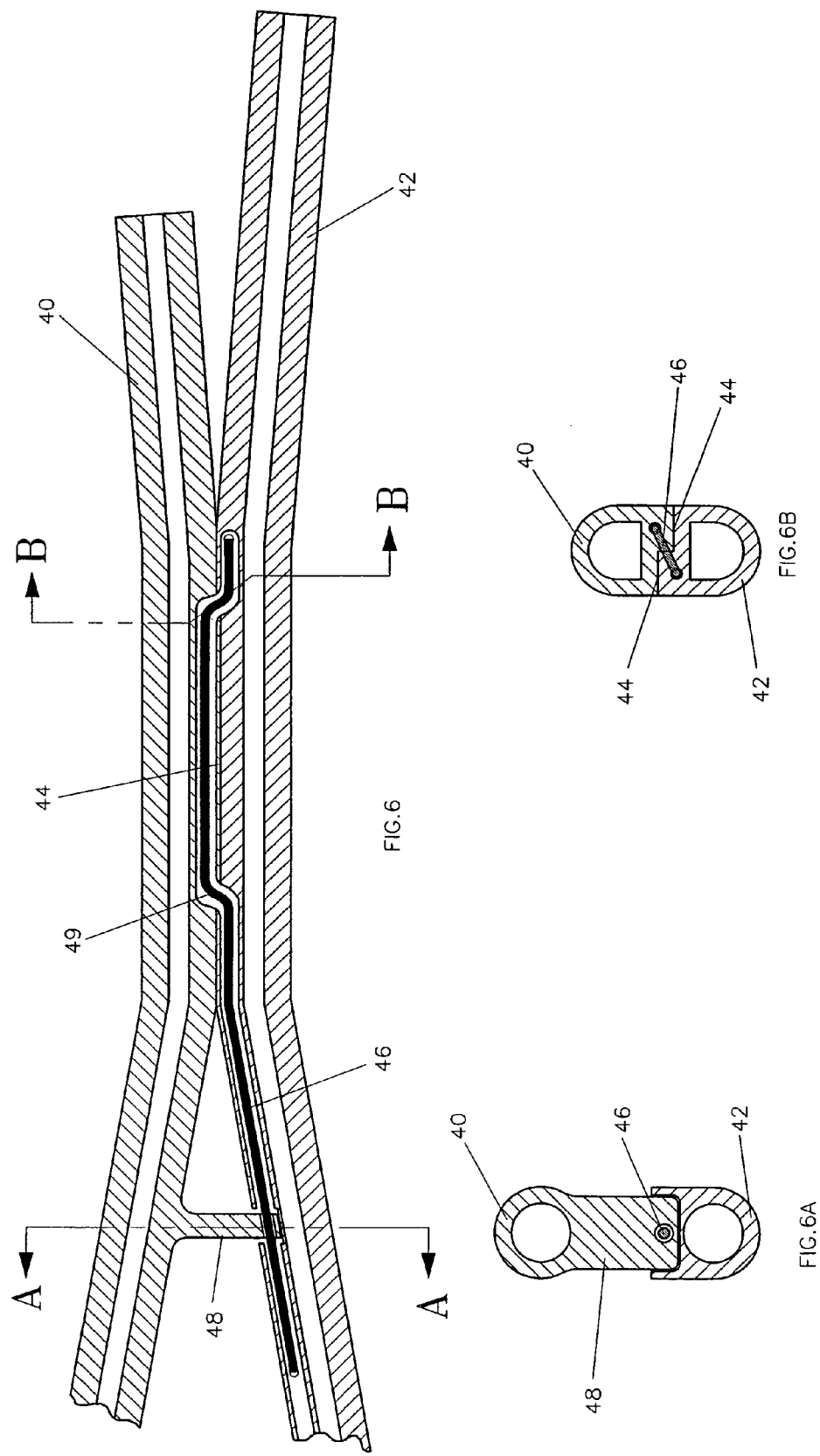

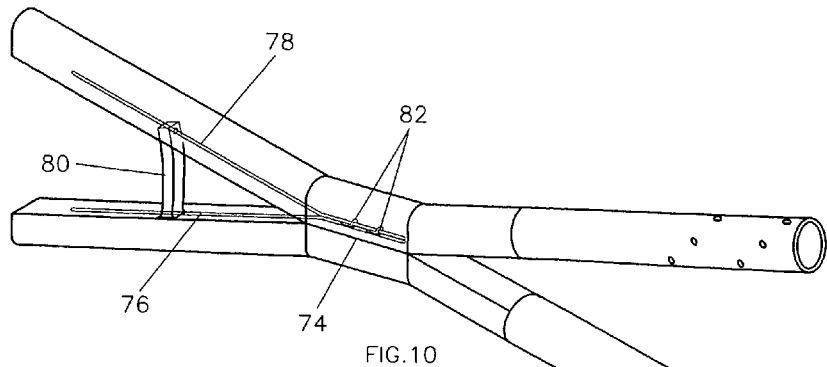
FIG.10
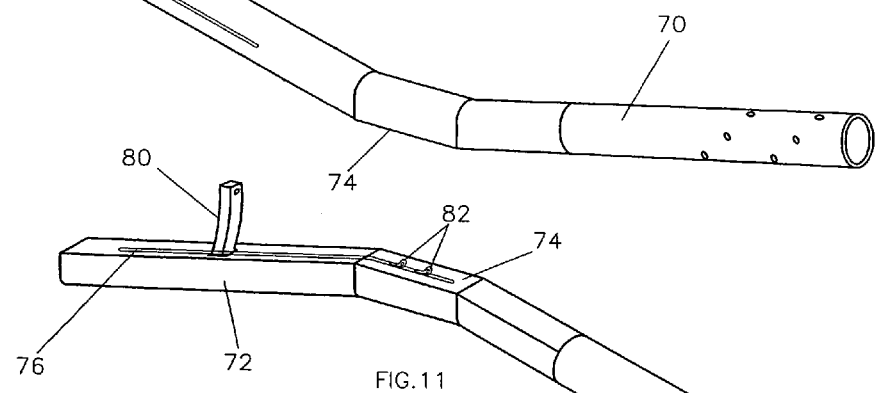
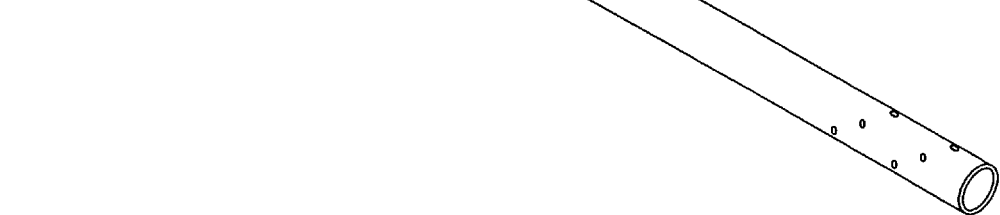
FIG.11

CATHETER RETENTION

BACKGROUND OF THE INVENTION

This invention relates in general to a device and method for retaining a catheter in a patient and more particularly to the retention of a dual tube hemo-dialysis catheter.

DESCRIPTION OF PRIOR ART

Dual tube hemo-dialysis catheters are used to provide long term access to the venous system. The catheter contains two lumens. One lumen for withdrawal, and one lumen for return blood flow. Hemo-dialysis filtration machines are connected to the catheter at regular intervals such as every other day. The patient's blood is removed, filtered, and returned to the patient. A catheter of this design is described by Ash et al. in U.S. Pat. No. 5,947,953. These catheters must be fixed to the patient to prevent the catheter from pulling out or advancing into the patient. The most common method is to tunnel the catheter from the point of venous access towards a remote location where the catheter is brought out of the skin. This tunnel may be from 5-20 cm long. A Dacron cuff attached to the catheter shaft is located within the tunnel. The cuff provides a porous area, which the patient's tissue grows into, providing an anchoring means. The cuff method is described by Martin et al. in U.S. Pat. No. 5,053,023. The catheter also may be sutured to the patient at the exit site by a "purse string" suturing technique.

Another method of fixing a catheter to the patient to prevent pulling out is to provide a bifurcation which is buried in the subcutaneous tissue. The bifurcate is located just outside of the catheters entrance to the vein. This design is described by Schon et al., in U.S. Pat. No. 5,718,692. The Schon catheter contains two tubes brought together to form a bifurcation. The proximal ends of the tube are split apart and are tunneled separately to a remote location where they are brought through the skin surface. The tissue between the proximal tube legs forms an anchor. If the catheter is pulled on, it cannot come out without pulling through the tissue. The catheter cannot advance due to the hub that joins the two tubes. This method provides better catheter retention than the tunneled and cuffed designs.

PROBLEMS WITH PRIOR ART

When it is desired to remove these catheters, which may be after a period of two years in place, both of the above discussed methods have their downfalls. In both cases, it is necessary to perform minor surgery to loosen the catheter. The tunneled and cuffed catheters require the cuff to be transected from the surrounding tissue. The bifurcated design requires the site above the bifurcation to be opened, the tissue carefully picked away from the catheter and the catheter to be removed in the reverse method from its installation. This is time consuming and dangerous. If the catheter is inadvertently cut, it can easily break during removal.

OBJECTS

Accordingly, it is a major object of this invention to provide a multiple tube catheter design, of which a hemo-dialysis catheter is a prominent example, wherein the catheter design provides an enhanced trade-off of effective anchoring in the patient with ease of removal by a doctor.

It is a related purpose of this invention to provide this ease of removal without requiring surgery to loosen the catheter for the purpose of removing the catheter.

It is a further related object of this invention to provide this improved multiple tube catheter in a design which readily adapts to currently employed techniques for catheter insertion.

It is a further related object of this invention to provide the above objects in a fashion that avoids substantial increased costs in product or procedure.

It is a further related object of this invention to provide the above objects in a device that does not require the cutting or dissection of tissue to remove the catheter and thus reduces the trauma and discomfort to the patient.

BRIEF DESCRIPTION

In brief, a multiple tube catheter is assembled so that in a zone of the catheter near the mid-point of the tubes, the tubes are longitudinally joined together. Along this zone, the sidewall of one tube is connected to the sidewall of the other. The attachment is achieved by a thread which in a preferred form is a wire. The wire attaches the two tubes together by a technique analogous to that of sewing or stapling or otherwise having the wire or thread extend between the sidewalls of the two tubes.

The proximal end of the thread or wire extends within the sidewall of one of the tubes to a point outside of the patient. Access can be had to the proximal end of the wire by the medical professional who can pull the wire free from the two tubes that are connected together by the wire. After the wire has been pulled free, the two tubes can be individually removed from the patient. This procedure requires little or no surgical removal or cutting of tissue.

In a preferred embodiment, the two tubes have adjacent flat surfaces and two threads or wires are used in parallel. In that preferred embodiment, a separating prong, slightly proximal of the attachment zone extends outwardly from the surface of one of the tubes to engage the surface of the other tube to force the tubes to diverge away from one another proximal to said zone. This assures that there is a predetermined bifurcation of the tubes within the patient's body thereby assuring that the tubes are adequately affixed and anchored in the patient and cannot be accidentally advanced or retracted. Growth of bodily tissues into the space between the tubes and the prong provides further anchoring.

DEFINITION

In preferred embodiments, a stainless steel surgical wire having a diameter of approximately 10 mils (0.010 inches) is used. However, elements other than a metallic wire can be used including, for example, a surgical suture.

Accordingly, it should be understood that in the claims, the term "wire" is used to cover not only the preferred metal wire but also whatever other sutures or threads or the like might be employed in the same or comparable geometric structures to hold the two tubes together in use and by withdrawal to permit parting of the two tubes when use is over.

BRIEF DESCRIPTION OF THE DRAWINGS

In FIG. 1, the tubes are brought exterior of the patient at points A. The two tubes are connected at a zone B.

FIG. 3 shows a wire 26 contained in the sidewall of the first tube 22, the wire being stitched into the sidewall of the second tube 20 in the area 24 where the two tubes are adjacent and stitched back into the sidewall of the first tube. FIG. 3 includes an expanded view of a small proximal segment of the sidewall of the tube 22 to more clearly show where the distal end of the wire 26 terminates within the sidewall; which is at a location exterior of the patient.

FIG. 4 illustrates the center segment of the FIG. 3 embodiment on a larger scale. FIG. 4 is a longitudinal sectional view and more clearly shows the wire 26 being stitched between the sidewalls of the two tubes 20, 22 and also shows the wire 26 extending through the end of the separating prong 28.

FIG. 4A is a cross-sectional view along the plane A-A of FIG. 4 and shows that two separate parallel wires 26 are employed. FIG. 4A is a cross-section through the separating prong 28 and shows that the wires are passed through the prong.

FIG. 4B is a cross-sectional view along the surface B-B of FIG. 2 and illustrates the stitching of the upper tube 20 to the lower tube 22 by the two wires 26.

FIG. 4C is a cross-sectional view of an alternative design separating prong 28 along plane A-A. FIG. 4C shows two wires 29 which reinforce the separating prong.

FIG. 5 illustrates a second embodiment of the invention. FIG. 5 is a longitudinal sectional view showing a wire 36 extending through a dove tail juncture 34 of the two tubes 30, 32.

FIG. 5A is a cross-sectional view along the plane A-A of FIG. 5 and illustrates an arrangement at that plane which is the same as that of the FIG. 4 embodiment.

FIG. 5B is a cross-sectional view along the plane B-B of FIG. 5 illustrating the two wires 36 that extend through the dove tail joining of the two tubes.

FIG. 6 is a longitudinal sectional view showing a third embodiment of this invention to which the two tubes 40, 42 are joined along a longitudinal lap joint 44. A single wire 46 is used to stitch the two tubes together.

FIG. 6A is a cross-section through the plane A-A of FIG. 6. This cross-section shows the separating prong 48 and illustrates that only one wire 46 is employed in this embodiment.

FIG. 6B is a cross-section along the surface B-B of FIG. 6 illustrating how the wire 46 that joins the two tubes together is threaded through the lap joint 44.

FIG. 9A is a cross-sectional view along the plane A-A of FIG. 9 and shows the wire 78 passing through an end of the separating prong 80.

FIG. 9B is a cross-sectional view along the surface B-B of FIG. 9 and shows a loop 82 which is attached to the loop wire 76 and loops around the anchor wire 78.

FIG. 10 is a somewhat fanciful transparent perspective view of the FIG. 9 embodiment to more clearly illustrate the loop and pin arrangement of coupling wires 76, 78 in the sidewalls of the two tubes 70, 72.

FIG. 11 illustrates what happens when the anchor wire 78 in the FIG. 9 embodiment is removed thereby uncoupling the anchor wire 78 from the loops 82 of the loop wire 76 so that the two tubes 70, 72 are no longer joined and can be removed from the patient.

DESCRIPTION OF THE PREFERRED EMBODIMENTS

Figure 1:
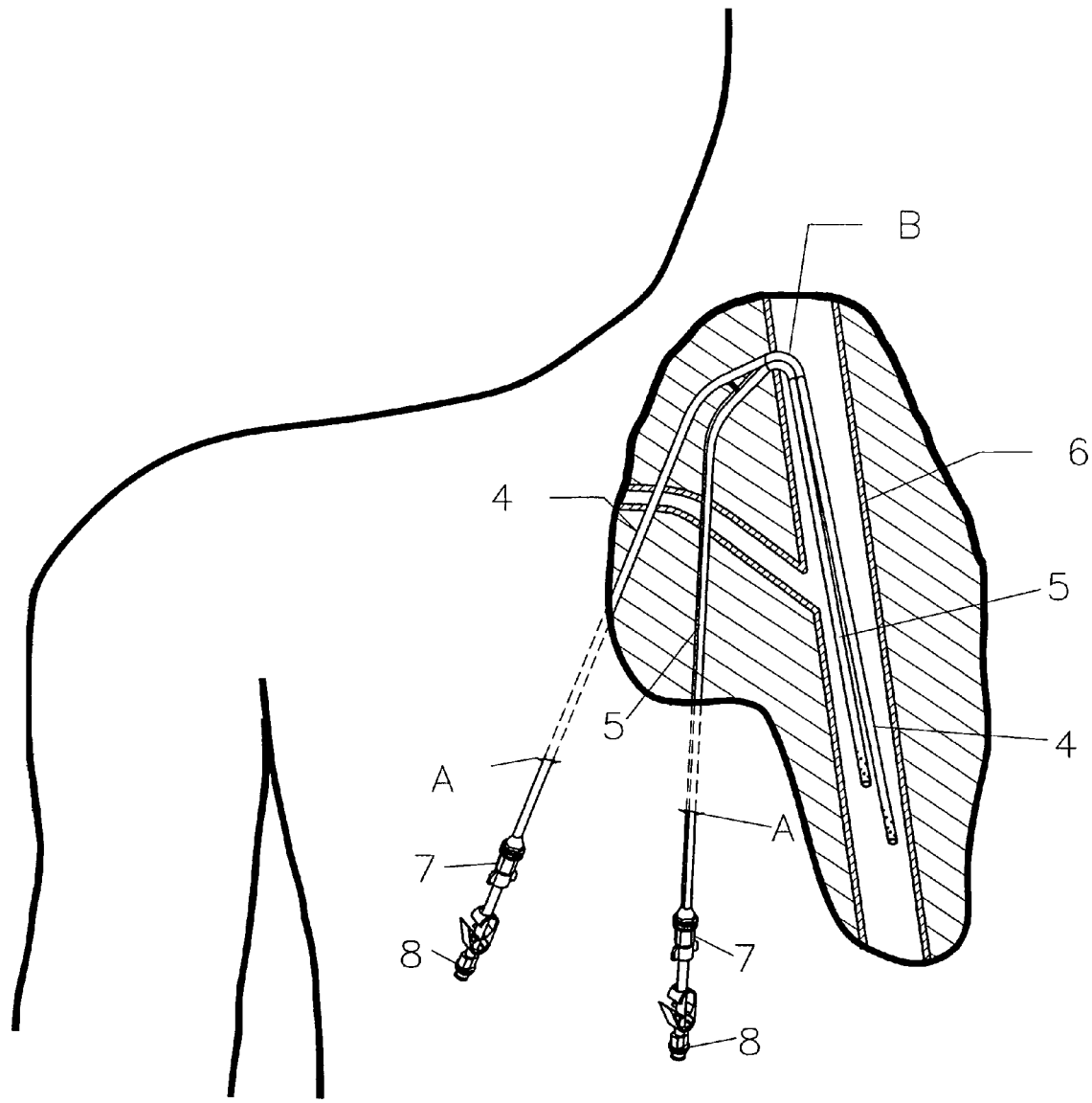
FIG. 1 schematically illustrates the positioning of a two tube hemo-dialysis catheter in the jugular vein.

FIG. 1 shows a first tube 4 and second tube 5 of a dual tube catheter placed in relative position in the jugular vein 6 of a patient. The two tubes 4, 5 emerge from the patient at the points A.

As is known in the art, various fittings 7, 8 are shown. The fittings 8 are used to connect the catheter to the rest of the dialysis processing system. Blood flow through the vein 6 is in a downward direction. The lumen in tube 4 is the return lumen and the lumen in tube 5 is the aspiration lumen. The technique of implanting this type of catheter is well known in the art and one technique is described in the Schon U.S. Pat. No. 5,718,692.

Figure 2:
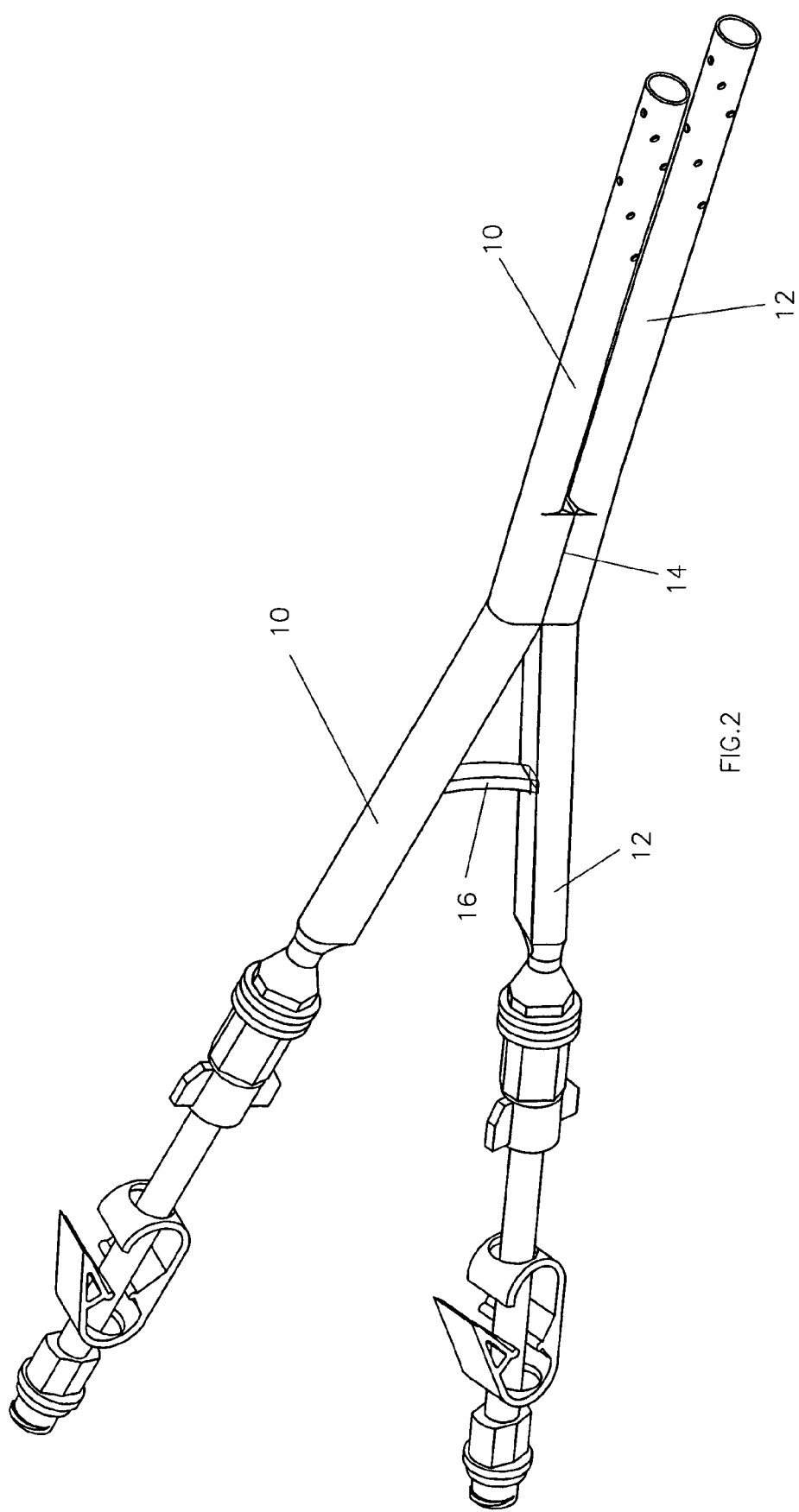
FIG. 2 is a perspective illustration of the invention showing the two tubes 10, 12 of the catheter which are in full contact with one another at a zone 14. A separating prong 16 is shown proximal of that zone.

FIG. 2 illustrates the catheter device of this invention generically in which a first tube 10 and a second tube 12 are joined together at a zone 14 by one of the techniques described herein. A separating prong 16 is positioned proximal of the zone 14 assuring an appropriate separation of the two tubes 10, 12.

Figure 3:
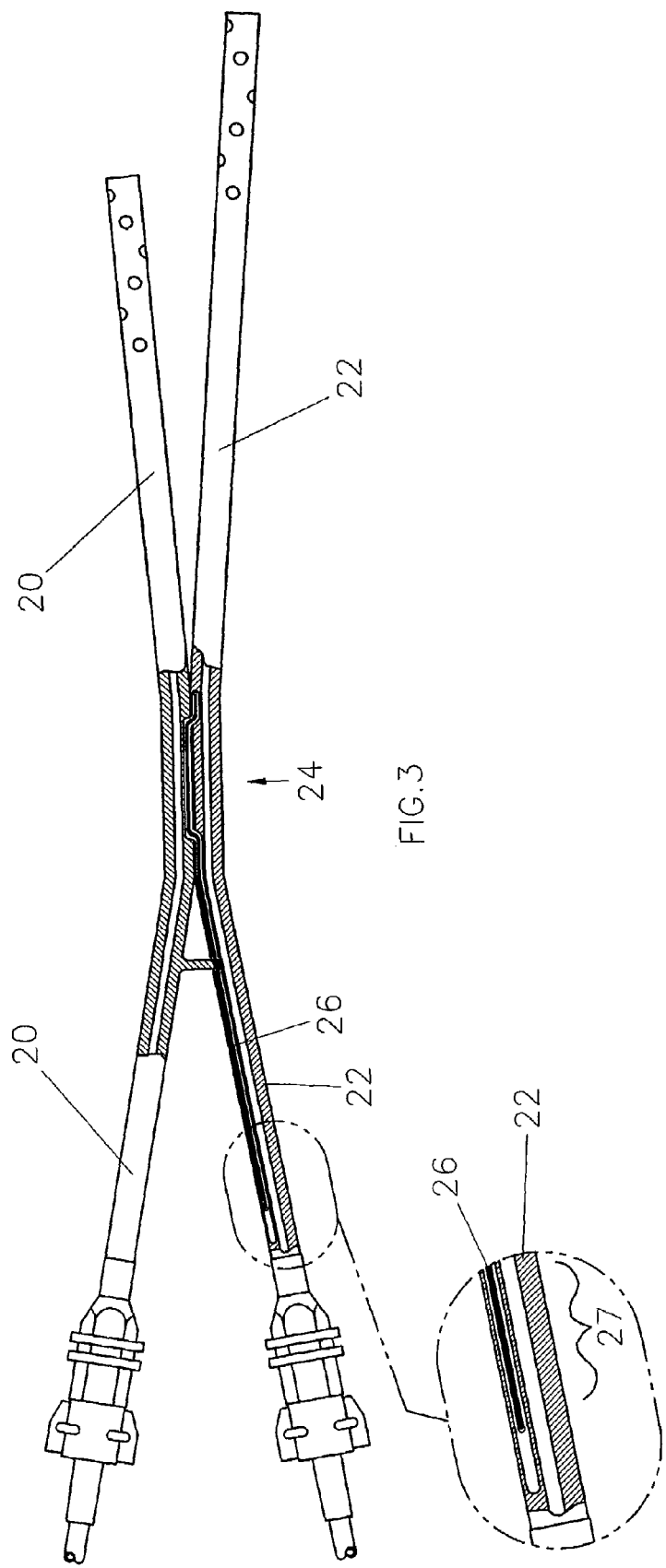
FIG. 3 is a perspective illustration of a first embodiment of this invention in which a center segment is shown in longitudinal section.

The embodiment shown in FIGS. 3 and 4 illustrates a first tube 20 and a second tube 22 joined together at a zone 24 by wires 26. FIGS. 3 and 4 show one of the two wires 26. Both of the wires 26 can be seen in the cross-sectional views of FIG. 4A and FIG. 4B. Each of the wires 26 extends within a proximal portion of the sidewall of the tube 22. Each wire 26 is threaded into the sidewall of the tube 20 and then back into the sidewall of the tube 22 so that the distal end of each wire 26 is embedded in the sidewall of the tube 22. In this fashion, the two tubes 20, 22 are held together by the two wires 26. FIG. 4C illustrates an alternative design prong 28 which is reinforced by two wires 29.

When the catheter is to be removed, access is had to the wires 26 at the proximal ends of the tubes 20, 22. The tube 22 is cut at the area 27 (see the expanded element in FIG. 3) so that access can be had to the proximal end of each wire 26. The wires 26 are pulled out of the tubes 20, 22 and must be pulled proximal of the opening 22R in the end of the separator prong 28. Once that has been done, the two tubes can be separately removed without requiring cutting a patient's tissue.

The separator prong 28 is a relatively thin flexible prong which will readily flex during removal without causing significant tissue trauma. It has an end which fits into recess 22R. The prong may be reinforced with metal to prevent tearing of the polyurethane.

As may be seen in FIG. 4B, the two tubes 20 and 22 are formed so that at the zone 24, they have flat surfaces which abut against one another.

As may be seen in FIGS. 2 and 4, the "bread-loaf" or tunnel like cross-section for the tubes 20 and 22 is maintained some distance proximal of the zone 24. The tubes 20, 22 transition to the usual circular cross-sections distal of the zone 24.

The separator prong 28 extends into the wall of the tube 22 at the recess 22R. The end of the prong 28 has two openings through which the wires 26 pass. This aids in maintaining rigidity for the prong 28 when the catheter is in use. The wires 26 have to be pulled proximally by at least enough to clear the prong 28 in order for the tubes 20, 22 to be fully separated.

FIG. 5 illustrates a second embodiment of the invention in which the two tubes 30, 32 are adjacent to one another along a zone 34 that provides a dove tail engagement between the two tubes. In this embodiment, the joining wires 36 extends through the teeth of both crenellated sections of the dove tail joint 34. The relatively thin flexible prong 38 extends from the wall of the tube 30 and has an end which fits into a recess in the wall of the tube 32. As in other embodiments, the joining wires 36 extend through openings in the end of the prong 38. The removal of the wires 36 and the separation of the tubes 30 and 32 is the same as in the embodiment of FIGS. 3 and 4.

The FIG. 6 embodiment is similar to the other embodiments in that there are two tubes 40, 42 having flat surfaces adjacent to one another along a zone 44 and having a separating prong 48. The key distinction in FIG. 6 is that the adjacent surface 44 is a longitudinal lap joint and there is only a single joining wire 46. The wire 46 is threaded between the two portions of the lap joint 44, as shown in FIG. 6B, in a fashion that means the wire 46 is, in this embodiment, not within a single longitudinal plane. The manner in which the wire 46 is threaded from the upper tube 40 into the lower tube 42 along the surface B-B is mirrored by the manner in which it is threaded from the lower tube 42 into the upper tube 40 at a position 49 proximal of the surface B-B.

Figures 7, 8:
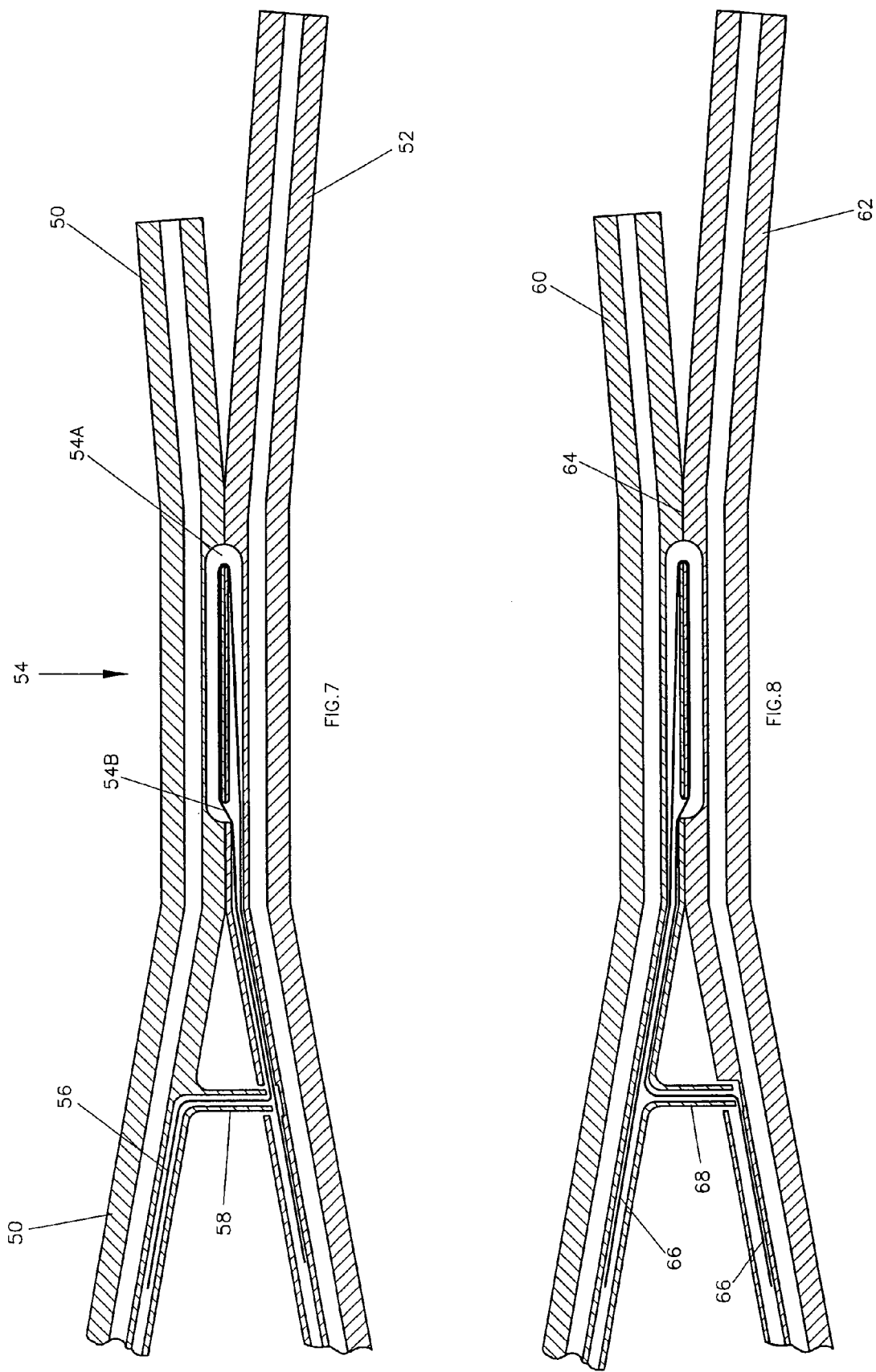
FIG. 7 is a longitudinal cross-sectional view of a fourth embodiment in which a suture 56 is used to stitch two tubes 50, 52 together at the zone 54 where they are adjacent to one another.
FIG. 8 is a longitudinal cross-sectional view of a fifth embodiment, similar to the fourth embodiment, where a suture 66 is employed in a fashion slightly alternate to that of FIG. 5 to stitch the two tubes 60, 62 together at the zone 64 where they abut one another.

FIGS. 7 and 8 indicate two other embodiments in which suture material capable of being used for surgical stitching is used. In FIG. 7, the suture 56 extends through the sidewall of the lower tube 52 to the zone 54 where the two tubes are adjacent to one another. At point 54A, the suture is threaded into the sidewall of the upper tube 50 to return proximally within the sidewall of the upper tube 50 until it exits at the point 54B. It passes within the sidewall of the lower tube 52, up through the prong 58 and then proximally through the sidewall of the upper tube 50.

The FIG. 8 embodiment is very similar to the FIG. 7 embodiment in which the upper tube 60 and lower tube 62 are joined together at the adjacent surface 64 by a suture 66 that doubles back within the wall of the upper tube 60; the one having the prong 68.

Figure 9:
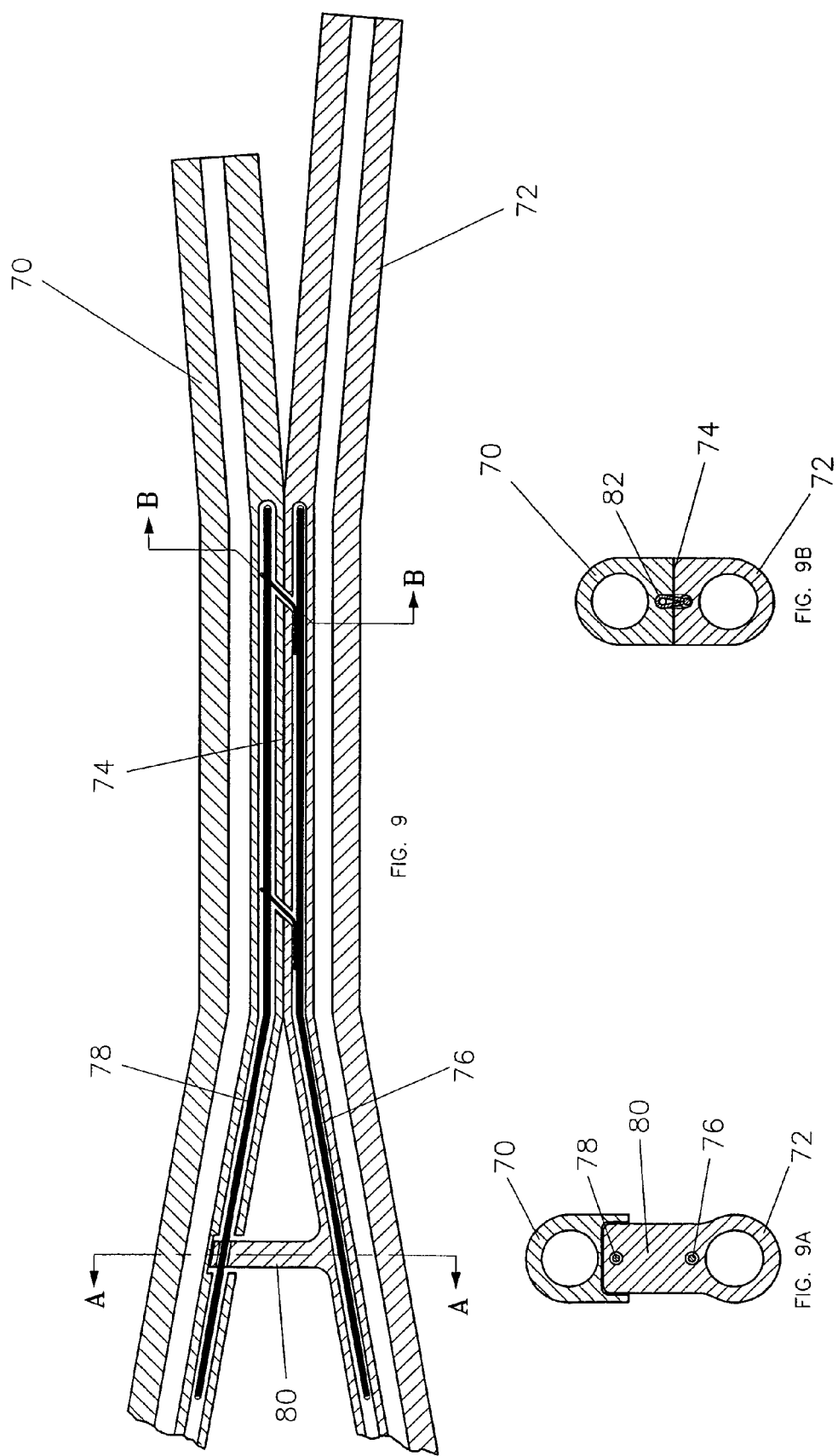
FIG. 9 is a longitudinal cross-sectional view of a sixth embodiment which employs a loop and pin method of coupling the wires 76, 78 in the sidewalls of the two tubes 70, 72 at the zone of juncture 74.

FIG. 9 illustrates a sixth embodiment in which first and second tubes 70, 72 are deployed adjacent to one another along flat faces 74. A first wire 76, called herein a loop wire, is contained in the wall of the tube 72. A second wire 78, called herein an anchor wire is contained in the wall of the other tube 70.

As may best be seen in FIG. 10, when the catheter is in use, the anchor wire 78 extends through two loops 82 which in turn are soldered to the loop wire 76. This connection holds the two tubes 70, 72 together because the wires 76, 78 are contained within the sidewalls of the tubes 70, 72.

When it is desired to remove the tubes from the patient, the two tubes are separated to facilitate such removal. The anchor wire 78, as illustrated in FIG. 11, is accessed by a medical professional and withdrawn from the tube 70. This disconnects the anchor wire 78 from the loops 82 and the two tubes 70, 72 can be separated and handled individually.

It might be noted, that the distal portion of the two tubes in each embodiment is circular in cross-section. To assure that the two tubes are adjacent to one another along a flat surface, the two tubes are formed to have a bread-loaf or tunnel-like cross-section in the zone of contact.

Numerous embodiments of this invention have been disclosed in order to illustrate the scope of the inventive concept. However, one skilled in the art can apply this concept to other embodiments.

For example, although it is clearly preferred that the tubes be adjacent along a flat surface, the inventive concept can be employed with two tubes in contact along a circular cross section and thus adjacent only along a line. Such an embodiment might require that the coupling wire or thread be exposed when extending from one tube to the adjacent tube.

In most embodiments, the preferred format is to have two wires or threads connecting the adjacent tubes. However, a single wire or thread can be used, although at the present time, such is not preferred in most embodiments.

In all embodiments, it is preferred as shown in FIG. 3, that the proximal ends of the wire are sealed into the catheter so that when the tubes are to be removed, the proximal ends of the tubes are cut at an appropriate point and access can be had to the wire to pull the wire free so that the tubes can be separated. This proximal sealing of the wire can be done after the wire has been threaded into the tubes.

Plastic tubes of the sort depicted in the various embodiments can be readily molded with the lumen depicted and with the longitudinal openings of the sidewalls for receipt of the wire. The wire is typically assembled in the two tubes by being passed through a longitudinal lumen within the sidewall of one tube and threaded into a similar lumen in the other tube. The wire and tubes are flexible enough so that this threading can be readily achieved.

In one typical embodiment, the following parameters are employed. The tubes are made of a polyurethane material and have a diameter of 120 mils and a sidewall thickness of 20 mils. The wire is spring temper stainless steel, Teflon coated. The wire ends are slightly tapered to create a stiffness transition. The longitudinal sidewall lumens to receive the wire are approximately 15 mils; enough to provide a very easy slip fit relationship with a 10 mil wire. The prong is 50 mils thick, by 70 mils wide and extends for a length of approximately 200 mils.

What we claim is:
1. A catheter assembly comprising:
one tube having a lumen and a sidewall, and
a longitudinal companion member,
said tube and said companion member coupled to and contacting one another at surfaces thereof along a predetermined zone, and
a linear engagement member extending longitudinally within said sidewall of said tube and through said companion member, without extending into the lumen of said tube, said tube and said companion member held together solely at said zone,
each of the distal most and proximal most ends of said linear engagement member being embedded in said sidewall of said tube,
said tube, said companion member and said linear engagement member extending proximal of said zone by an amount sufficient to extend out of the body of a patient in whom the catheter is implanted, said linear engagement member being accessible upon cutting through said sidewall within which said linear engagement member is embedded, thereby permitting withdrawal of said linear engagement member to cause said tube and said companion member to disconnect and permit separate, independent withdrawal of said tube and said companion member from a patient.

2. The catheter assembly of claim 1 further comprising:
a flexible separating prong extending outward from the surface of one of said tube and said companion member to abut the surface of the other at a location proximal of said zone to force said tube and said companion member to diverge proximal of said zone.

3. The catheter assembly of claim 2 wherein: said surfaces at said zone are flat surfaces.

4. The catheter assembly of claim 3 wherein: said linear engagement member is a set of two wires.

5. The catheter assembly of claim 2 wherein: said linear engagement member is a set of two wires.

6. The catheter assembly of claim 2 further comprising:
a recess on the surface of said tube or said companion member against which said prong abuts, said recess engaging the abutting end of said prong.

7. The catheter assembly of claim 6 wherein: said linear engagement member extends through said prong.

8. The catheter assembly of claim 2 wherein: said zone is located on a portion of the catheter that is located within a patient when the catheter is implanted in a patient.

9. The catheter assembly of claim 1 wherein: said surfaces at said zone are flat surfaces.

10. The catheter assembly of claim 9 wherein: said linear engagement member is a set of two wires.

11. The catheter assembly of claim 1 wherein: said linear engagement member is a set of two wires.

12. The catheter assembly of claim 1 wherein: said zone is located on a portion of the catheter that is located within a patient when the catheter is implanted in a patient.

13. The catheter assembly of claim 1 wherein: said linear engagement member is a surgical suture.

14. A catheter assembly comprising: at least one tube comprising a lumen, and a longitudinal companion member coupled to and contacting one another at surfaces thereof along a predetermined zone, said tube and said companion member each having a sidewall, a wire extending longitudinally within said sidewalls of each of said tube and said companion member, without extending into the lumen of said tube and passing through surfaces of said tube and said companion member at said zone to hold said tube and said companion member together at said zone, said tube and said companion member being held together solely at said zone, said tube, said companion member and said wire extending proximal of said zone by an amount sufficient to extend out of the body of a patient in whom the catheter is embedded, said surfaces at said zone being flat surfaces, said wire being accessible upon cutting through said sidewall within which said wire is embedded, thereby permitting withdrawal of said wire to cause said tube and said companion member to disconnect and permit separate, independent withdrawal of said tube and said companion member from a patient, a flexible separating prong extending outward from the surface of one of said tube and said companion member to abut the surface of the other at a location proximal of said zone to force said tube and said companion member to diverge proximal of said zone, and a recess on the surface of the other of said tube or companion member against which said prong abuts, said recess engaging the abutting end of said prong.

15. A dialysis catheter assembly comprising: first and second tubes, each tube comprising a lumen, each having a sidewall, and a linear engagement member extending longitudinally within said sidewalls of each of said tubes without extending into the lumens of said tubes, engaging said tubes and holding said tubes in contact at a predetermined zone, said tubes being held together solely at said zone, each of the distal most and proximal most ends of said linear engagement member being embedded in at least one of said sidewalls of said tubes, said tubes and said linear engagement member extending proximal of said zone by a length sufficient to extend out of the body of a patient in whom the catheter is implanted, whereby cutting a proximal length of those of said tubes containing said proximal end of said linear engagement member provides access to said linear engagement member so that withdrawal of said linear engagement member will cause said tubes to disconnect and permit separate, independent withdrawal of said tubes from a patient.

16. The catheter assembly of claim 15 further comprising:
a flexible separating prong extending outward from the surface of one of said tubes to abut the surface of the other at a location proximal of said zone to force said tube and said companion member to diverge proximal of said zone.

17. The catheter assembly of claim 16 further comprising:
a recess on the surface of said tube or said companion member against which said prong abuts, said recess engaging the abutting end of said prong.

18. The catheter assembly of claim 15 wherein: said linear engagement member is a set of two wires.

19. The catheter assembly of claim 15 wherein: said zone is located on a portion of the catheter that is located within a patient when the catheter is implanted in a patient.

\* \* \* \* \*